(12) United States Patent
Watson et al.

(10) Patent No.: US 11,710,420 B1
(45) Date of Patent: Jul. 25, 2023

(54) DERIVATIVE CONTENT CREATION USING NEURAL NETWORKS FOR THERAPEUTIC USE

(71) Applicant: X Development LLC, Mountain View, CA (US)

(72) Inventors: Philip E. Watson, Felton, CA (US); Julia Watson, Felton, CA (US); Kathleen Watson, Sunnyvale, CA (US); Christian Ervin, Burlingame, CA (US)

(73) Assignee: X Development LLC, Mountain View, CA (US)

( * ) Notice: Subject to any disclaimer, the term of this patent is extended or adjusted under 35 U.S.C. 154(b) by 492 days.

(21) Appl. No.: 16/720,884

(22) Filed: Dec. 19, 2019

(51) Int. Cl.
*G09B 19/00* (2006.01)
*G16H 20/70* (2018.01)
*G06N 3/08* (2023.01)

(52) U.S. Cl.
CPC ............... *G09B 19/00* (2013.01); *G06N 3/08* (2013.01); *G16H 20/70* (2018.01)

(58) Field of Classification Search
CPC ............ G09B 19/00; G16H 20/70; G06N 3/08
See application file for complete search history.

(56) References Cited

U.S. PATENT DOCUMENTS

| 10,091,326 | B2 | 10/2018 | Rietveld et al. |
| 2004/0128624 | A1 | 7/2004 | Arellano et al. |
| 2011/0213197 | A1 | 9/2011 | Robertson et al. |
| 2012/0265616 | A1 | 10/2012 | Cao et al. |
| 2013/0262365 | A1 | 10/2013 | Dolbear et al. |
| 2013/0283162 | A1 | 10/2013 | Aronsson et al. |
| 2016/0225187 | A1 | 8/2016 | Knipp et al. |
| 2019/0042908 | A1 | 2/2019 | Garcia |
| 2019/0156222 | A1 | 5/2019 | Emma et al. |

OTHER PUBLICATIONS

Bowman et al., "Generating Sentences from a Continuous Space", arXiv:1511.06349v4 [cs.LG] May 12, 2016.

*Primary Examiner* — James B Hull
(74) *Attorney, Agent, or Firm* — Christensen O'Connor Johnson Kindness PLLC

(57) ABSTRACT

A technique for dynamic generation of a therapeutic derivative story includes obtaining attribute data that describes characteristics of a content consumer along with situational details describing an emotional situation involving the content consumer. A relatability score for the therapeutic derivative story is determined. A content data structure (CDS) is selected. The CDS specifies story elements of a preexisting story. The story elements are associated with metadata constraints that constrain modification or use of the story elements. The metadata constraints indicate whether associated ones of the story elements are mutable story elements. One or more of the mutable story elements are adapted based on the attribute data or the situational details as constrained by the metadata constraints and to an extent determined at least in part by the relatability score to generate the therapeutic derivative story.

21 Claims, 8 Drawing Sheets

US 11,710,420 B1

DERIVATIVE CONTENT CREATION USING NEURAL NETWORKS FOR THERAPEUTIC USE

TECHNICAL FIELD

This disclosure relates generally to automated content creation, and in particular but not exclusively, relates to personalized content creation for therapeutic use.

BACKGROUND INFORMATION

The beneficial use of stories, whether fictional or factual, for therapeutic use is known. Stories can help an individual see their own personal story or situations through a new lens while maintaining a sufficient comfort distance from their own life story. Stories can help reframe a struggle or ground the emotional side of a struggle in a relatable context. The effectiveness of stories to help individuals process a personal struggle, dilemma, challenge, or emotion is correlated to how relatable the story is to the individual's own situation and life story.

Many struggles that we all experience over the course of our lives are similar to the struggles experienced by those who have come before us. As such, people have written stories about these struggles, which can be beneficial to those newly presented with a similar struggle, but perhaps in a different context. The contextual differences may be superficial (e.g., at a different point in history, in a different age of life, in a different culture, in a different geographical setting, between individuals in a different social hierarchy, etc.), but the underlying struggle may be similar or even identical. The contextual differences in our common life stories can reduce relatability for an individual, which can suppress the emotional responses to watching, listening to, or reading another's story. These emotional responses can be vital to leveraging the therapeutic use of others' stories.

Unfortunately, stories are fixed in expression (e.g., in a medium) that is typically unchangeable. As such, many stories that are used for therapeutic advantage, are not as effective as they could be, if the contextual specifics of that story were more identifiable and relatable to the individual seeking insight and self-reflection from the life experiences of others.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
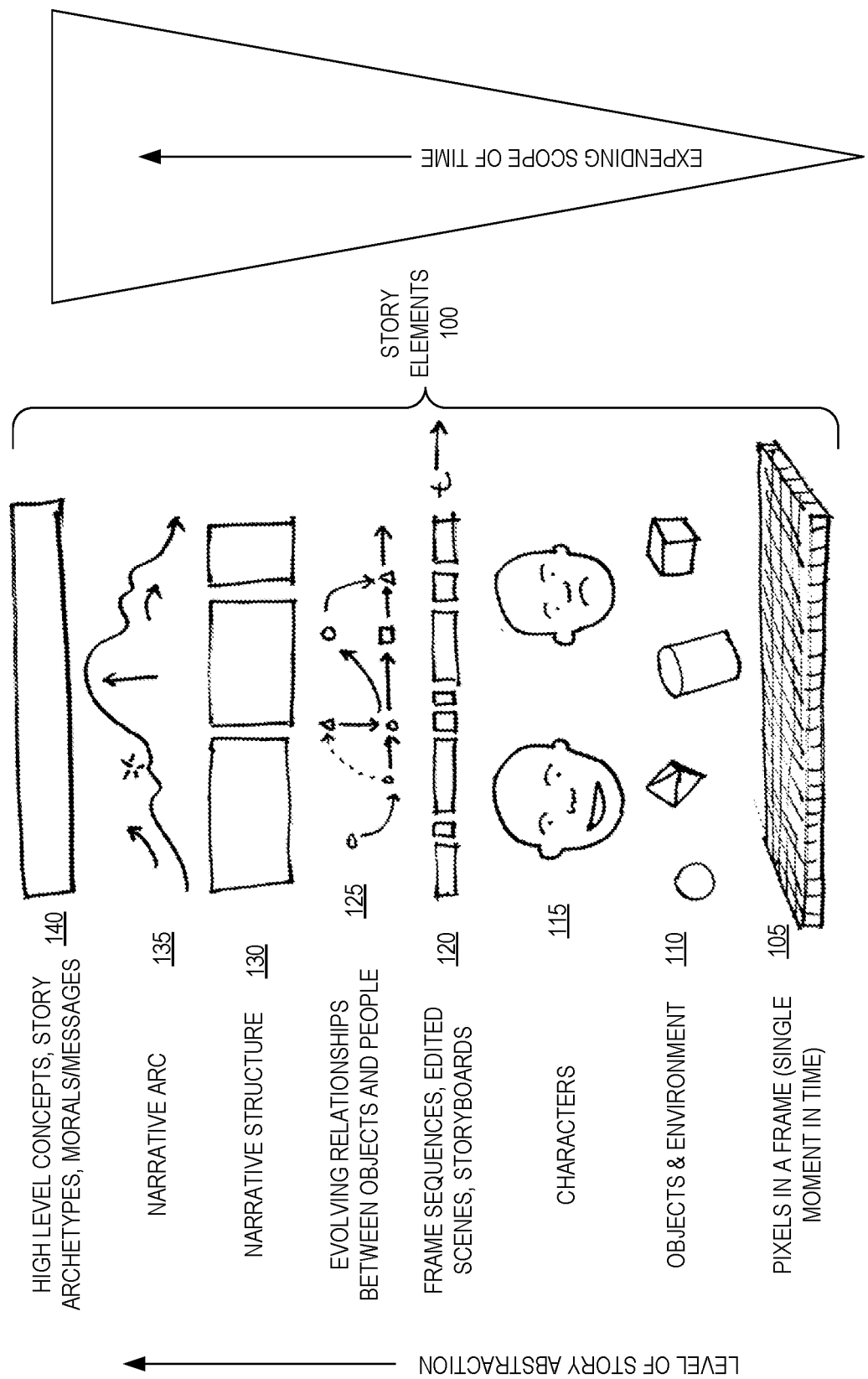
FIG. 1 illustrates demonstrative story elements of a story described at different levels of story abstraction, in accordance with an embodiment of the disclosure.

Embodiments of a system and methods of operation for dynamically creating personalized therapeutic derivative stories are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments disclosed herein describe a dynamic content generation system that can ingest existing content (e.g., stories) and use a trained artificial neural network (ANN) to generate derivative stories by modifying story elements to suit a content consumer's (e.g., end user's) needs. A particularly beneficial subset of derivative stories are therapeutic derivative stories that aid the content consumer in coping with or otherwise working through an emotional situation. The dynamic content generation system is customizable with a therapy module to create such therapeutic derivative stories that are personalized based upon the characteristics of the content consumer, situational details describing an emotional situation involving the content consumer, and even the comfort level the content consumer has with the emotional situation.

The system generates therapeutic derivative stories using existing stories as a guide, seed, or inspiration. The therapeutic derivative stories may be fictional, factual (e.g., news, documentaries, etc.), or a combination of both. The therapeutic derivative stories may be in a variety of mediums or formats including video stories, audio stories, textual stories, pictorial stories, or combinations thereof. For example, the dynamic content generation system can take the plot of a particular story and generate a new derivative story, with new or modified story elements, that follows the same plot. Story elements (e.g., objects, environments, characters, frame sequences, narrative structure, narrative arc or plot, or high-level concepts) from different existing stories can be mixed, matched, substituted, or newly generated to create therapeutic content. An organized collection of story elements forms a story, such as a therapeutic story.

The therapeutic derivative stories generated by the dynamic content generation system may be used for therapeutic purposes that reframe an emotional situation in a beneficial way to lead to better emotional or mental outcomes of the content consumer. For example, the therapeutic derivative stories may help a content consumer (or group of content consumers) safely experience or reexperience an emotional situational (e.g., how to cope with a past traumatic event, how to prepare for a future challenging event, etc.). In yet other embodiments, the therapeutic derivative stories may provide the end user with a tool for scenario development and presentation. In other words, as part of a therapeutic process, the therapeutic derivative stories may be used for role playing scenarios resulting from potential decisions or actions and how those decisions/actions could play out. The individual scenarios may be stored as generalized templates that may be customized with the characteristics of the end user and situational details related to the end user's specific emotional situation (e.g., environment, age, etc.).

The dynamic content generation system may be used individually by the end user for personal growth and therapy. Alternatively, the dynamic content generation system may be used corporately with a group of individuals sharing common attributes or situational details to remind the individuals in the group that other people have had a similar experience and their struggles/emotions have commonality with others living through a similar experience. In some cases, the dynamic content generation system may be a tool used by a therapeutic influencer, such as a parent/guardian, a teacher, a mentor, a coach, a therapist, or other generalized counselors. In yet other embodiments, the therapeutic derivative stories may be used for educational or training purposes. For example, police or firefighter academies may use the dynamic content generation system to help prepare and acclimate these public safety officers for potential high stress, emotional situations.

The dynamic content generation system described herein is different from conventional tools or materials, which merely relate a generalized situational story that is not well tailored, personalized, or customized to an audience or content consumer. In most cases, in order for a therapeutic story to be capable of providing beneficial feedback, it must be relatable. The more personalized the therapeutic story, the more relatable it is, and thus the material has a greater likelihood of eliciting an emotional response. As such, there is a direct correlation between relatability and the ability of a particularly therapeutic story to evoke an emotional response, which helps expose and process the underlying emotional situation (exposure therapy). Accordingly, the dynamic content generation system is capable of generating customized therapeutic derivative stories that may be similar to existing stories in certain respects, but which are populated or reskinned with personalized details of the end user and the end user's situation to improve relatability. These customized details may be gradually adapted over a period of time (e.g., during the telling of a particular therapeutic derivative story or between different viewing instances) to ratchet up relatability at a controlled rate to elicit emotional response while maintaining a safe or healthy proximity from particularly traumatic details.

The therapeutic derivative stories may be created with new or modified story elements extracted or modified from other existing stories, or entirely created anew. The therapeutic derivative stories created herein may range from relatively minor changes to constituent story elements of an existing story, to radical changes to and/or combinations of existing stories or story elements such that the newly created therapeutic derivative story would be virtually unrecognizable to a human reader and merely tangentially derived from one or more story elements of one or more pre-existing stories. In many cases, these therapeutic derivative stories may be thought of as machine learning (ML)-generated stories.

In yet another aspect, the dynamic content generation system contemplates a content marketplace of reuseable and extensible content data structures describing existing stories and story elements. These existing stories or story elements are created by authors, therapists, or other counselors and made available to the dynamic content generation system for inclusion in dynamically generated therapeutic stories. These existing stories or story elements may include copyrighted content that the system tracks for royalty fees when incorporating the copyrighted content in dynamically created derivative content. These and other features are described below.

FIG. 1 illustrates story elements 100 of a story described at different levels of story abstraction, in accordance with an embodiment of the disclosure. A story may be factual, fictional, or combinations thereof. It may be presented in a video format, an audio format, a textual format, a pictorial format, or combinations thereof. A story is an organized collection of story elements 100. Story elements 100 may be described at different levels of story abstraction from the low-level elements (abstraction level 105) all the way up to high level concepts (abstraction level 140). It should be appreciated that FIG. 1 is merely demonstrative and not intended to be an exclusive list of types of story elements or levels of abstraction. It is further anticipated that the illustrated abstraction levels may be blended in various combinations.

Abstraction level 105 includes story elements such as pixels or sounds that exist in a single frame or at a single moment in time. Abstraction level 110 includes objects and environments that exist within a story over longer periods of time, such as scenes, chapters, or even the whole story. Abstraction level 115 includes characters, including their personalities, appearances, and other attributes. Abstraction level 120 includes frame sequences, edited scenes, or storyboard descriptions. Abstraction level 125 includes descriptions of the evolving relationships between objects and people. These evolving relationships may be thought of as emotional or relational story arcs between characters and objects/environments. Abstraction level 130 includes the narrative structure of the story. The narrative structure may be a 24 hour episode that follows a character for 24 hours and the conflict and resolutions that occur in that 24 hour window. In another example, the narrative structure may be a school year where the story opens with the first day of school and concludes with the last day of the school year along with the events that transpire over the course of that school year. Abstraction level 135 includes the narrative arc of the story. The narrative arc is a higher level story shape describing the order of conflicts and resolutions between the characters, objects, or environment of the story (e.g., a specific plot). Finally, abstraction level 140 includes the high-level concepts such as story archetype, moral, or message. The story archetype represents the general plot type, of which there are many recognized types. Some common plot types include: a quest, a voyage and return, overcoming a monster, a comedy, a tragedy, a rebirth, and rags to riches.

Story elements 100 all represent different pieces of a story described at different levels of precision and abstraction. As the abstraction levels rise the scope of time occupied by these story elements expands. For example, a single image pixel may only exist for a single frame in time while the moral or archetype are expressed by the story as a whole. Changes in story elements 100 at one level may have a ripple effect to changes in different abstraction levels. In particular, changes in higher abstraction levels may often ripple into lower abstraction levels. For example, selection of a different story archetype may often lead to different narrative arcs, evolving relationships, and characters.

The above described story elements 100 may be distinctly identified and parsed in autonomous or semi-autonomous manners. For example, software can easily identify distinct image frames and pixels from time stamps and pixel order or physical locations. Image, shape, or voice recognition techniques may be used to identify distinct characters and objects. Frame sequences may be identified from hard breaks in images or other computation video editing techniques. Identification of higher level story elements is expected to be accomplished with machine learning that leverages various deep neural networks. Such neural networks may include trained artificial neural networks (ANNs) such as generative adversarial networks (GANs) or variational autoencoders that are trained using large datasets of preexisting stories.

Figure 2:
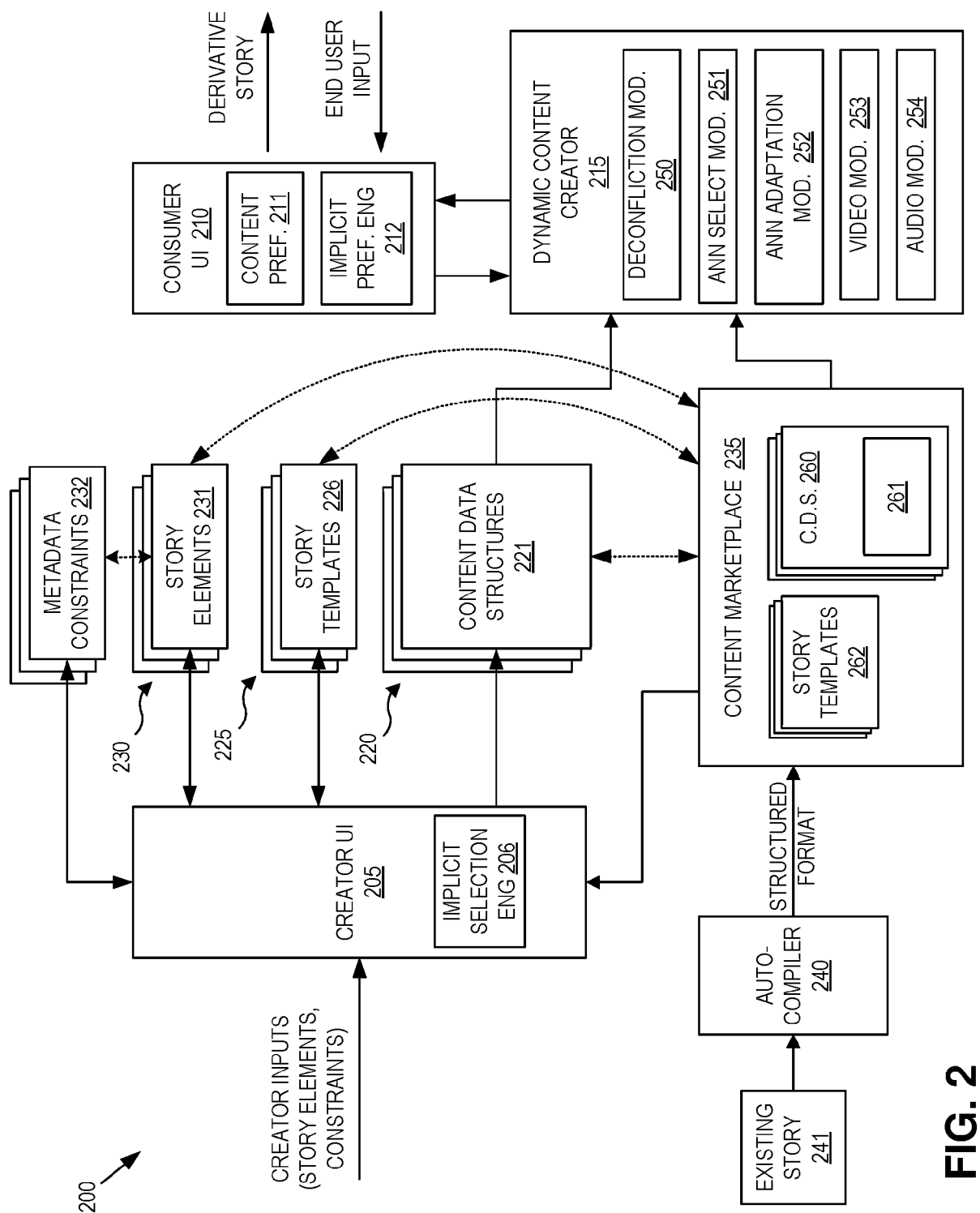
FIG. 2 is a functional block diagram illustrating a system for dynamic generation of derivative stories, in accordance with an embodiment of the disclosure.

FIG. 2 is a functional block diagram illustrating a system 200 for dynamic generation of derivative stories (including therapeutic derivative stories), in accordance with an embodiment of the disclosure. The illustrated embodiment of system 200 includes a creator user interface (UI) 205, a consumer UI 210, a dynamic content creator 215, a library 220 of content data structures (CDS) 221, a library 225 of story templates 226, a library 230 of story elements 231, metadata constraints 232, a content marketplace 235, and an autocompiler 240. The illustrated embodiment of dynamic content creator 215 includes a deconfliction module 250, an ANN select module 251, an ANN adaptation module 252, a video module 253, and an audio module 254. The illustrated embodiment of content marketplace 235 includes CDS 260, constraint metadata 261, and story templates 262.

Creator UI 205 is a software portal or application that enables a content creator (e.g., creator side end user) to create or manipulate story elements 231 along with metadata constraints 232 that describe how the corresponding story elements 231 may be subsequently modified or used. The story elements 231 and metadata constraints are populated into a CDS 221, which associates metadata constraints 232 with their story elements 231. Each content data structure 221 may be thought of as a repository for storing the story elements 231 and metadata constraints 232 of a given story, or portion thereof. CDS 221 are reusable and extensible data structures that may link to other CDS 221 (referred to as secondary CDS) to build out or complete a story. In other words, a CDS 221 may be populated with the story elements describing only a story portion or sub-component (e.g., a single character, a particular environment, etc.) that may be incorporated into a larger story by linking multiple CDS 221. In one embodiment, CDS 221 are extensible markup language (XML) files.

Figure 3A:
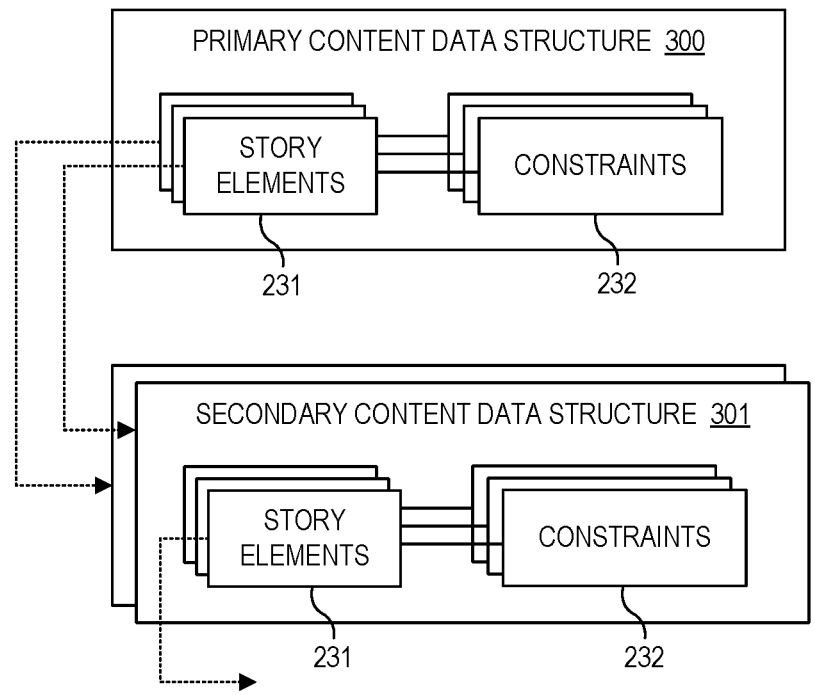
FIG. 3A illustrates a primary content data structure linked to secondary content data structures, in accordance with an embodiment of the disclosure.

CDS 221 may be categorized into two types—primary CDS and secondary CDS. Primary and secondary CDS are similar data structures except for their hierarchical position in describing an overall story. FIG. 3A illustrates how a primary CDS 300 includes story elements 231 associated with metadata constraints 232. Some of the story elements 231 are linked to secondary CDS 301 also having story element 231 and associated metadata constraints 232. Primary CDS 300 may be thought of as containing the higher abstraction level story elements (e.g., story archetype, narrative arc, narrative structure, description of how the relationships between particular characters evolve, etc.), and may also define some story elements at lower story abstraction levels. Secondary CDS 301 may be thought of as mainly containing lower abstraction level story elements (e.g., character descriptions, objects, environments, etc.), but may also include higher abstraction level story elements. These lower abstraction level story elements may be populated into a story described by primary CDS 300 via linking or reuse. For example, primary CDS 300 may include an undefined or partially defined character that is populated or "skinned" by a secondary CDS 301. Alternatively, primary CDS 300 may include a fully defined story element (e.g., character) that is designated as a mutable story element by its corresponding metadata constraints 232. This mutual story element may be adapted (e.g., modified or swapped out) for another character defined in another secondary CDS 301. The linking of secondary CDS 301 may continue for multiple levels to build up complex, detail rich stories that are extensible in virtually limitless combinations.

Both primary CDS 300 and secondary CDS 301 are reusable in that a content creator may create a story element, such as a character, environment, object, plot, etc., in isolation without specifically associating the story element with a complete story. In particular, content marketplace 235 may be a repository for a broad array of CDS 260 describing story elements specifically intended for integration into derivative stories. In other words, some of CDS 260 may describe copyrighted story elements. In this scenario, content marketplace 235 may track royalty fees for the use, adaptation, and/or integration of copyrighted story elements into derivative stories. CDS 260 may include metadata constraints 261 at the option of the content owners to ensure reuse or modification of their copyrighted story elements complies with their own terms or standards. For example, characters written for children may be precluded from integration into adult stories, violent stories, or otherwise. Metadata constraints 261 may further constrain how a copyrighted character may be used in a derivative story by constraining the type of evolving relationships that may be used in connection with the copyrighted character. Thus, metadata constraints 232 (or 261) may place constraints that affect how the story element may be adapted with other story elements defined at the same or different level of story abstraction.

Metadata constraints 232 may constrain the use of story elements 231 in a variety of ways. In one embodiment, story elements 231 may be defined as mutable story elements (e.g., changeable, replaceable, or omittable) or immutable story elements (e.g., fixed elements of a story). For example, a content creator may create a rich and detailed story using a primary CDS 300 and linking to many secondary CDS 301. The content creator may then flag certain core story elements which the content creator believes are fundamental to the essence of the story as immutable. Other story elements 231 that are less fundamental may be tagged as mutable story elements that can be adapted or swapped out with another story element by dynamic content creator 215 at the time of rendering a derivative story. The mutable story elements may be fully fleshed story elements, or mere placeholder elements intended to be populated with a preexisting story element defined in a secondary CDS 301 that is selected by dynamic content creator 215 based upon content preferences of a content consumer. The adaptation of a mutable story element (whether a fully fleshed element or a placeholder element) is defined and constrained by its associated metadata constraints 232.

Figure 3B:
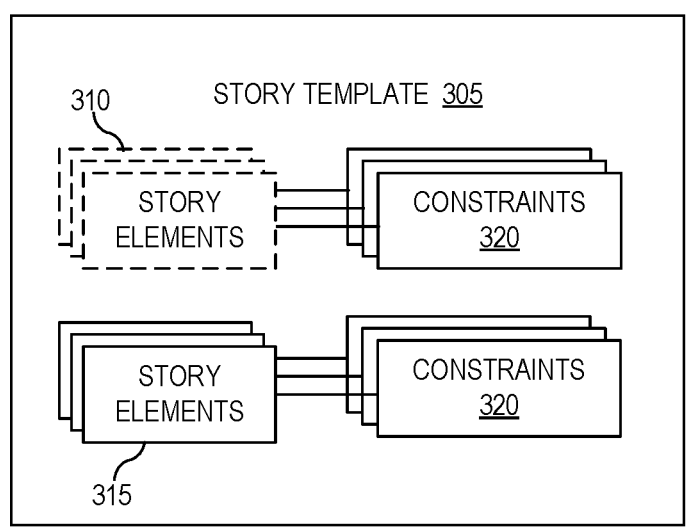
FIG. 3B illustrates a story template including mutable story elements, immutable story elements, and metadata constraints constraining the modification or use of the story elements, in accordance with an embodiment of the disclosure.

Creator UI 205 may also provide a content creator with access to library 225 of story templates 226 from which to select. Story templates 226 streamline the creation of new CDS 221 and provide the content creator a framework or structure for inputting story elements 231 using creator UI 205. For example, a story template 226 may be created for each story archetype, or for creating a new character, a new object, a new environment, etc. FIG. 3B illustrates an example story template 305 that is prepopulated with mutable story elements 310, immutable story elements 315, and metadata constraints 320, in accordance with an embodiment of the disclosure. Immutable story elements 315 are defined as fixed or unchangeable in one or more respects by their corresponding constraints 320. In the example of an archetype template, the specific archetype may be defined as immutable. The mutable story elements 310 may be mere placeholder story elements to be populated by the content creator. The content creator may author an entirely new story element into a mutable story element 310, or link to an existing story element 231 (e.g., one defined by a CDS 260 within content marketplace 235). It should be understood that the metadata constraints 320 associated with a mutable story element 310 may place certain constraints on how the mutable story element 310 may be adapted or populated.

Creator UI 205 may be implemented as a UI tool that explicitly solicits the content creator to select story templates 226, input story elements 231, input associated metadata constraints 232, or otherwise. However, in some embodiments, creator UI 205 may include an implicit selection engine 206 that uses artificial intelligence (AI) algorithms to analyze the content creator's initial inputs (e.g., initial story elements) or past interactions with creator UI 205 to understand the type of story the content creator is beginning to create. From these initial story elements and past interactions, the implicit selection engine 206 may offer up suggestions of similar or related story elements 226 that may be incorporated into the content creator's new story. Implicit selection engine 206 may learn the behaviors, selections, interests, story types, and/or genres that a particular content creator generates or typically operates in, and thus automatically suggest certain story templates 226 or story elements 226. Accordingly, implicit selection engine 206 may provide various levels of automated help, whether explicit or implicit, to the content creator while creating a new story or CDS 221.

The illustrated embodiment of system 200 further includes an auto-compiler 240 for ingesting an existing story 241 into content marketplace 235. In other words, auto-compiler 240 represents tools for parsing existing story 241 into its constituent story elements each described at various levels of story abstraction and creating CDS 260 for reuse or adaptation into derivative stories. These ingested existing stories 241 may be finished stories (e.g., fully rendered or embodied), or alternatively, skeleton stories (e.g., not fully rendered or fully embodied) that represent partial stories or broad outlines of stories with several aspects left unfinished to be completed and custom rendered at the time of viewing by the end user. Auto-compiler 240 may include autonomous or semi-autonomous software tools including one or more ANN to parse story elements out of an existing story and create CDS 260. Image/shape recognition, voice recognition, and various computational video editing tools may be used as well for parsing story elements.

Consumer UI 210 is a software portal or application that enables a content consumer (e.g., viewer or listener end user) to input content preferences 211 into system 200. Content preferences 211 may be solicited by consumer UI 210 and indicate preferences of the content consumer for specific characteristics to be represented in a derivative story. For example, content preferences 211 may include identification of at least one of a format type for the derivative story, a time constraint for consuming the derivative story, a genre of the derivative story, a setting or location for a story (e.g., space, underwater, jungle, etc.) a theme of the derivative story, a character for inclusion in the derivative story, a cultural adaptation for the derivative story, a subject matter maturity rating for the derivative story, a subject matter for the derivative story, a moral/lesson for the derivative story to teach, or otherwise. Consumer UI 210 interfaces with dynamic content creator 215 to provide content preferences 211 thereto and display, or otherwise output, the derivative story generated by dynamic content creator 215 to the content consumer. These derivative stories may be new derivative stories that aren't recognizable to the content creator, modified lengths of existing stories to suite time constraints of the content consumer, a transformation of an existing story from one medium (e.g., video) to another medium (e.g., audio story), or otherwise.

Dynamic content creator 215 uses content preferences 211 received from the content consumer to select one or more CDS 221 that describe story elements, which may be adapted and/or combined in a manner consistent with content preferences 211 to generate a new derivative story. In one embodiment, dynamic content creator 215 creates a new derivative story that is personalized to the desires or needs of an individual end user and does so in real-time or near real-time at the point of consumption. In other words, the derivative stories are generated and fixed just-in-time for consumption in an adaptable and personalized manner. Generation and adaptation of an existing story defined in a CDS 221 (or 260) is accomplished by dynamic content creator 215 based on both the end user's content preferences 211 and the metadata constraints 232 (or 261) constraining how story elements 231 within the CDS may be modified or replaced.

The illustrated embodiment of dynamic content creator 215 includes ANN select module 251. ANN selection module 251 is a trained neural network (e.g., GAN, variational autoencoder, etc.) that selects one or more CDS 221 from library 220 or one or more CDS 260 from content marketplace 235 that are suitable based upon content preferences 211 provided by the content consumer. In other words, the ANN select module 251 is a neural network trained to identify potentially suitable candidate stories described in CDS 221 (or 260) when fed content preferences 211, which may form the basis for generating a derivative story. ANN selection module 251 may be implemented with other types of machine learning (ML) classifiers as well. In one embodiment, consumer UI 210 may provide the content consumer a list of available options that align with content preferences 211. The content consumer may then select the desired existing story, which will be a seed for a derivative story along with the selected CDS 221 and content preferences 211 that inform the modifications and adaptations to the seed story.

The illustrated embodiment of dynamic content creator 215 also includes deconfliction module 250. Deconfliction module 250 analyzes content preferences 211 for requests that may conflict with metadata constraints 232 (or 261) within CDS 221 (or 260). Example conflicts may be requests for copyrighted content that includes constraints preventing combinations or modification also requested by the content consumer. If conflicts are identified, deconfliction module 250 may seek to identify alternative CDS 221 that align with content preferences 211. Otherwise, deconfliction module 215 may request the content consumer to modify their content preferences 211.

ANN adaptation module 252 uses content preferences 211 provided by the end user to modify one or more selected CDS 221 (or 260) to generate a personalized derivative story. ANN adaptation module 252 is a trained neural network (e.g., GAN, variational autoencoder, etc.) that has been trained to create or derive new stories from existing stories (e.g., existing CDS 221 or 260) that are modified, skinned, or otherwise adapted based upon content preferences 211. For example, the content consumer may request characters from one story be inserted into the narrative arc of a second story while using the environment of yet a third story. ANN adaptation module 252 may also be trained to convert between formats (e.g., movie into a podcast, video story into an audio story, etc.), condense or expand a story, or otherwise.

In one embodiment, ANN adaptation module 252 is seeded with content preferences 211 and accesses library 220 and/or content marketplace 235 to mix and match preexisting stories to create a derivative story according to the end user's requests. In one embodiment, ANN adaptation module 252 is limited to using the CDS 221 (or 260) selected by ANN select module 251.

Finally, video module 253 and audio module 254 represent the various applications, codecs, and drivers to render the derivative story created by ANN adaptation module 252.

Consumer UI 210 may be implemented as a UI tool that explicitly solicits the content preferences 211 to aid in the creation of derivative stories. However, in some embodiments, consumer UI 210 may include an implicit preferences engine 212 that also uses AI algorithms to identify and analyze various sources of content preferences 211, whether explicitly or implicitly provided. Implicit sources of content preferences 211 may be gathered as initial content preference inputs, past content preference inputs, past interactions with consumer UI 210, past stories consumed by the end user, the content consumer's age, gender, location, cultural identifications, etc. In one embodiment, the end user may provide consumer UI 210 access to his/her calendar from which implicit preferences engine 212 may learn behavioral patterns, interests, time constraints (e.g., length of a commute) or otherwise, and use this data to formulate implicit content preferences 211 that are used to seed dynamic content creator 215. Accordingly, implicit preferences engine 212 may learn the behaviors, characteristics, interests, needs, situation, etc. of a particular content consumer, and automatically gather/generate content preferences 211. Implicit preferences engine 212 may provide various levels of automated help with the gathering and creation of content preferences 211. In one embodiment, consumer UI 210 may operate as (or transition to operating as) an autonomous or semi-autonomous portal for viewing derivative content with little to no explicit solicitation or querying of the content consumer.

FIG. 2 illustrates a software architecture for the various functional components of system 200. The functional blocks and connecting lines are intended to illustrate functional elements and interrelations, which may be localized in a single hardware system (e.g., computer), distributed across multiple hardware systems and interconnected via a network, or reside partially or entirely in cloud based computing systems that are accessed by an end user (e.g., content creator or content consumer) via a web browser or other client-side portals. In one embodiment, creator UI 205 or consumer UI 210 are installed on the end user's computing device while the other functional components (e.g., content marketplace 235 and dynamic content creator 215) are cloud-based. In yet other embodiments, all or some of the components of dynamic content creator 215 may be installed on the client-side and may even be incorporated within consumer UI 210. The functional components may be interconnected and distributed in other manners than strictly illustrated in FIG. 2.

Figure 4:
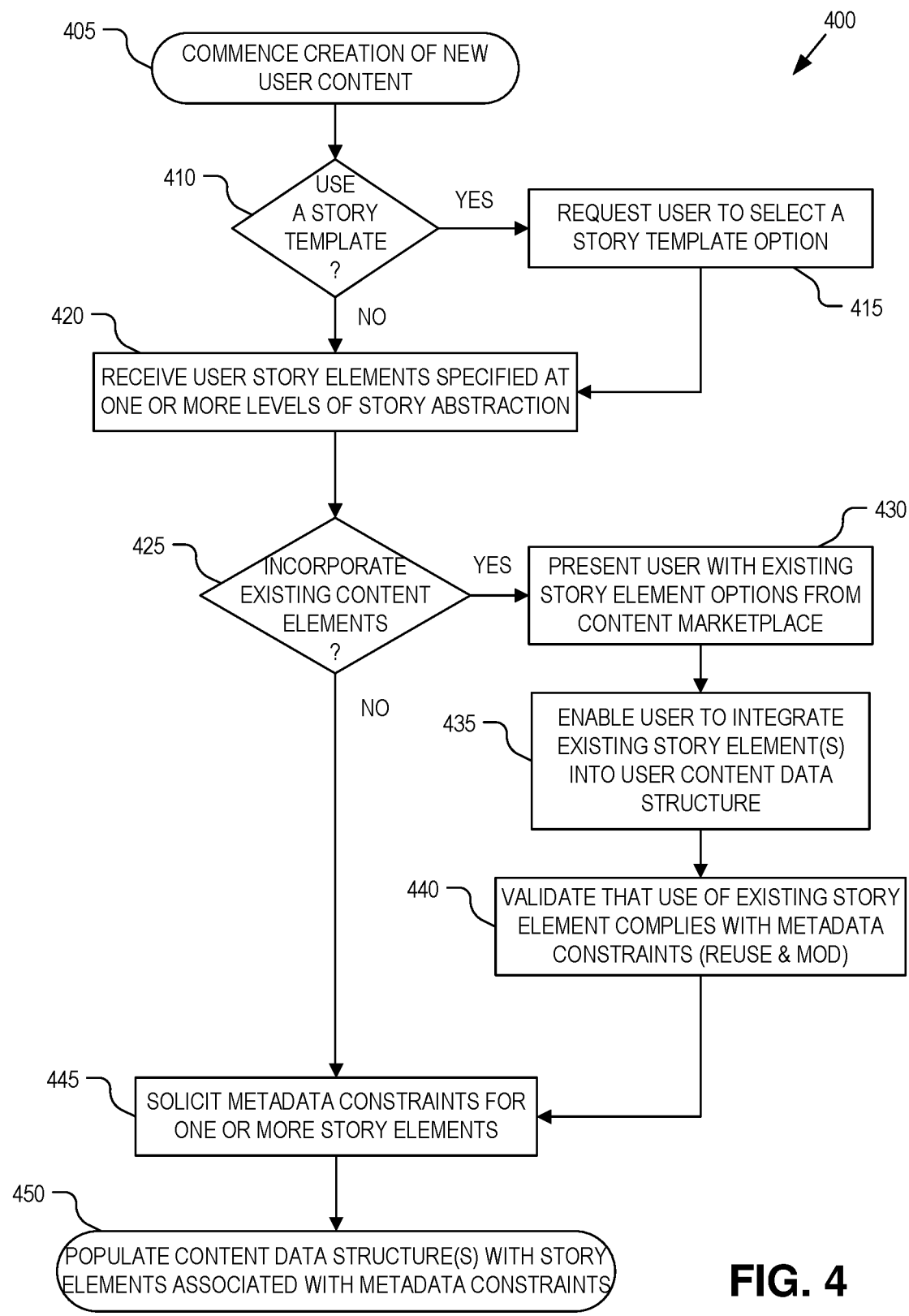
FIG. 4 is a flow chart illustrating a process for generating content data structures, in accordance with an embodiment of the disclosure.

FIG. 4 is a flow chart illustrating a process 400 for generating CDS 221, in accordance with an embodiment of the disclosure. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

Process 400 begins at process block 405 using creator UI 205. The content creator is given the option of creating a new story from a blank slate or using a story template as a beginning point (decision block 410). If the content creator opts to use a story template 226, then the content creator may browse library 225 via creator UI 205 to identify and select a suitable story template 226 (process block 415). In some embodiments, implicit selection engine 206 may aid the user in identifying story templates 226 and/or existing story elements 231 that may be helpful for the creation of new content.

In a process block 420, the content creator may commence inputting their story elements into creator UI 205, either with or without use of a story template 226. If a story template 226 is being used, as illustrated FIG. 3B, story template 305 may include mutable story elements 310 and immutable story elements 315. Some of these story elements may be prepopulated while others are blank fields that solicit user input. The story elements input by the user may be textual, video, graphical, audio, or otherwise in nature. Furthermore, the input story elements may be described at any one of the different levels of story abstraction described in connection with FIG. 1.

While the content creator is free to author as much of the story as desired, system 200 also provides the content creator the option to populate story elements with existing story elements already defined and described in secondary CDS 301. Should the content creator choose to use existing content (decision block 425), then creator UI 205 presents the content creator with a library 230 of existing story elements 231. Optionally, creator UI 205 may also present the content creator with options from content marketplace 235 (process block 430). The content creator can then incorporate existing story elements into their own CDS 221 via linking to one or more secondary CDS 301, thereby providing a quick option to build out story elements rich with details.

When linking to an existing story element, creator UI 205 analyzes the metadata constraints 232 (or 261) of the existing story element to ensure that applicable constraints on reuse and modification provided by the content owners or creators of the existing content are followed (process block 440). If the proposed use does not comply, then creator UI 205 blocks the combination.

In a process block 445, creator UI 205 solicits the content creator enter their own metadata constraints associated with the story elements of their story. The solicitation may be an explicit request, or an implicit request at the option of the content creator. In process block 450, the assembled story elements 231 and associated metadata constraints 232 are populated into a new primary content data structure and optional secondary content data structures depending upon the make up and structure of the story. The content data structure may then be saved locally for individual use and/or consumption, or submitted to content marketplace 235 to be shared with others, either freely or for profit.

Figure 5:
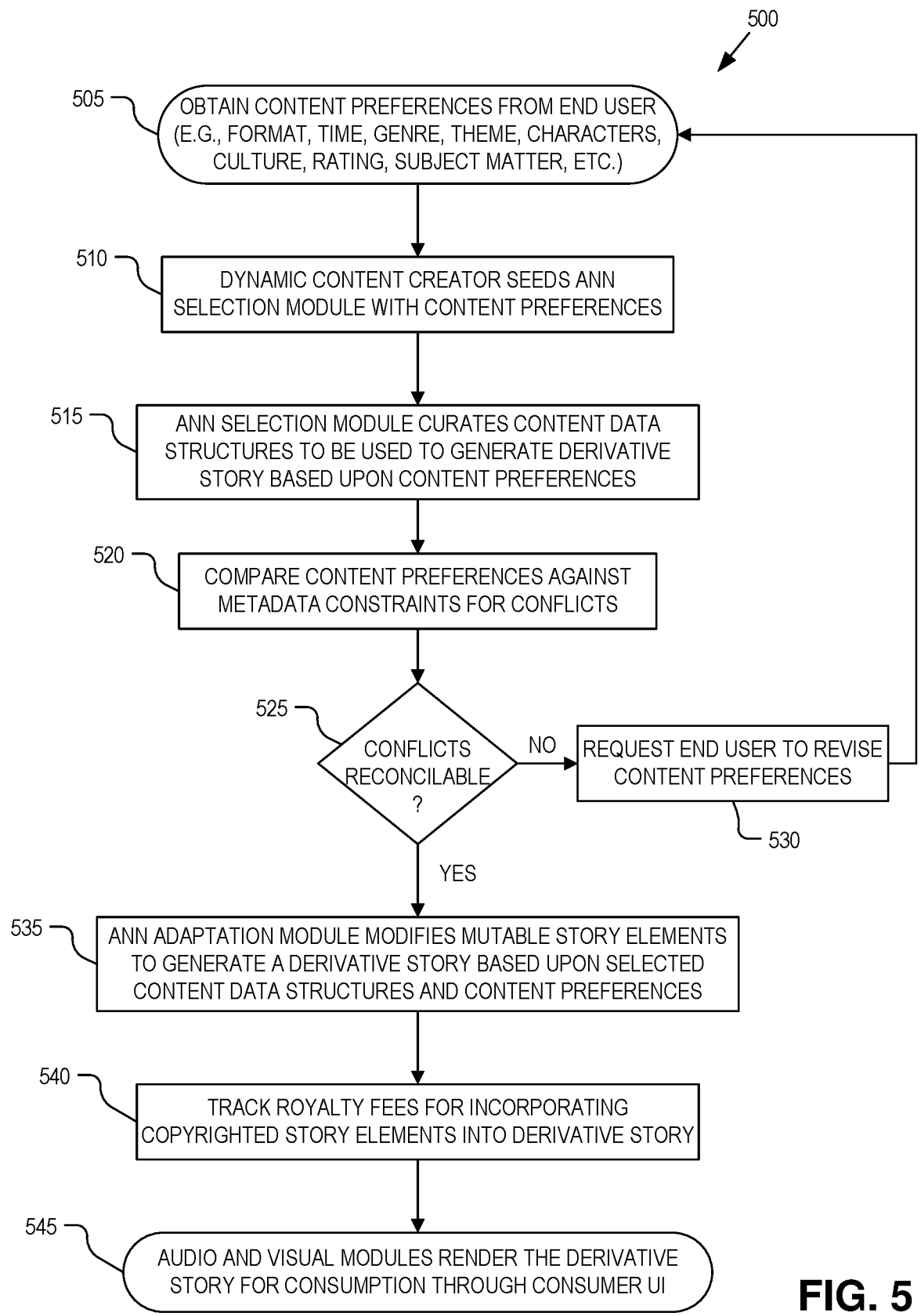
FIG. 5 is a flow chart illustrating a process for dynamic generation of a derivative story based upon one or more content data structures, in accordance with an embodiment of the disclosure.

FIG. 5 is a flow chart illustrating a process 500 for dynamic generation of a derivative story based upon one or more CDS 221 (or 260), in accordance with an embodiment of the disclosure. The order in which some or all of the process blocks appear in process 500 should not be deemed limiting. Rather, one of ordinary skill in the art having the benefit of the present disclosure will understand that some of the process blocks may be executed in a variety of orders not illustrated, or even in parallel.

In a process block 505, content preferences 211 are obtained by consumer UI 210 from the end user (e.g., content consumer). The content preferences indicate preferences for characteristics of a derivative story that the end user desires to consume. The content preferences may include identification of at least one of a format type for the derivative story, a time constraint for consuming the derivative story, a genre of the derivative story, a theme of the derivative story, a character for inclusion in the derivative story, a cultural adaptation for the derivative story, a subject matter maturity rating for the derivative story, a subject matter for the derivative story, or otherwise. The capture of content preferences 211 may be fully explicit (e.g., explicit end user queries), fully implicit (e.g., generated by implicit preferences engine 212 based on past end user interactions or permitted access to other user data), or a combination of both.

Content preferences 211 are used to identify one or more existing stories from library 220 or content marketplace 235 as defined in CDS 221 or 260. The identification and selection may be executed by seeding ANN selection module 251 with content preferences 211 (process block 510) to perform automated curating of the available CDS options based upon content preferences 211 (process block 515). In one embodiment, the content consumer can directly select a specific story (e.g., CDS) via consumer UI 210.

In a process block 520, content preferences 211 are compared against the metadata constraints of the curated CDS to identify any conflicts. Conflicts may arise between the preferences for characteristics in the derivative story and metadata constraints on the modification or use of the story element specified in the curated CDS. If the conflicts are irreconcilable (decision block 525), then consumer UI 210 requests the end user to revise their content preferences 211 (process block 530). However, if there are no conflicts, or the conflicts are reconcilable, then process 500 continues to a process block 535.

In process block 535, ANN adaptation module 252 adapts mutable story elements of the one or more selected CDS to the content preferences 211 of the content consumer as constrained by the metadata constraints of the selected CDS to generate a derivative story. The adaptation may be achieved by populating, replacing, or modifying the mutable story elements with story elements from other CDS located in library 220 or content marketplace 235. If copyrighted story elements are used from content marketplace 235, then royalty fees are obtained and tracked (process block 540). Examples of adaptation include populating a character story element with the character from another story, swapping environments (e.g., changing an underwater story to a deep space story), reskinning cultural characteristics of the environment, characters, or objects, or otherwise. Modifications may also be performed to elongate or condense a story by eliminating narrative arc story elements flagged as mutable or optional. Finally, in a process block 545, the derivative story generated by ANN adaptation module 252 is rendered by video module 253 and/or audio module 254 for consumption by the end user through consumer UI 210.

Figure 6:
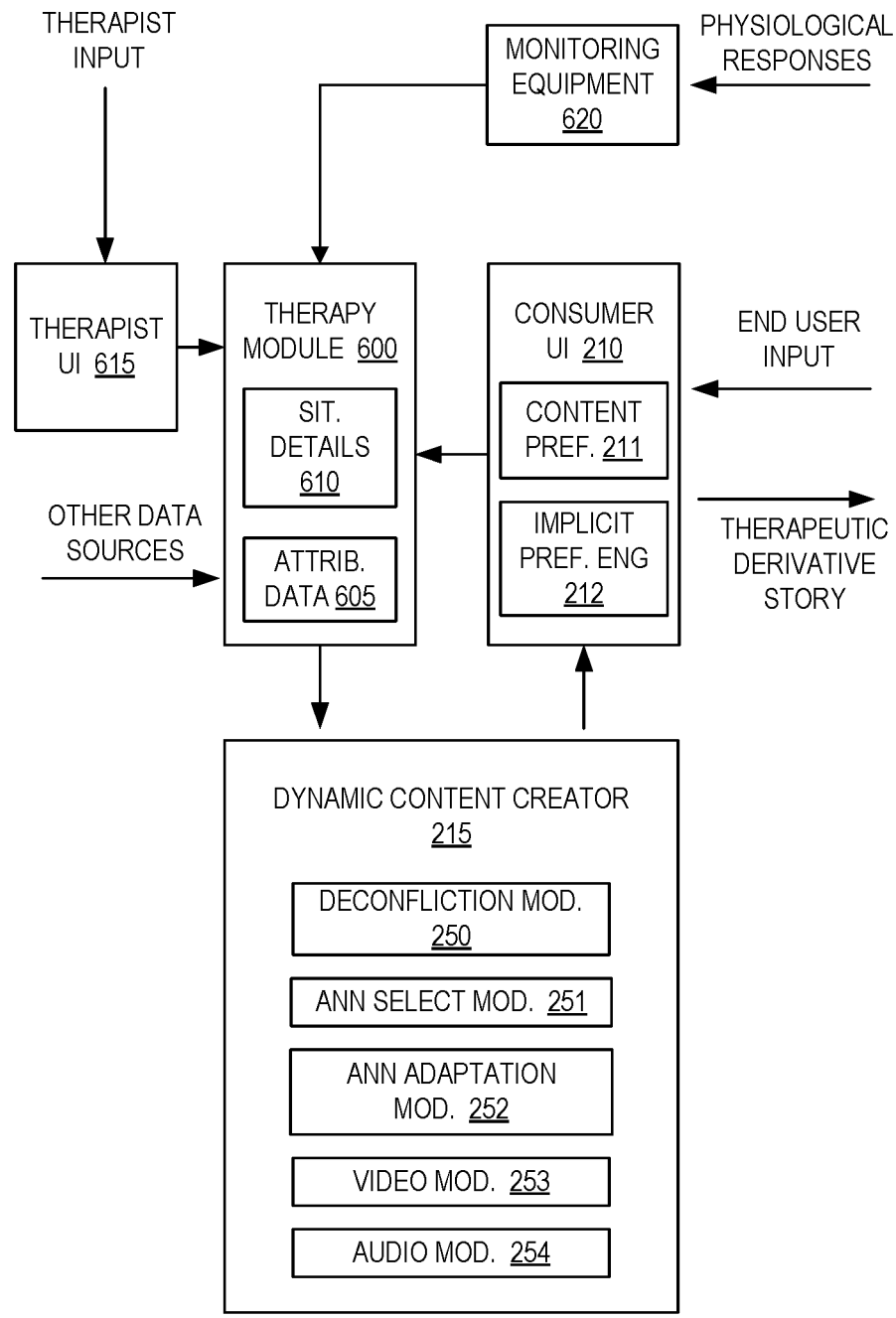
FIG. 6 is a functional block diagram illustrating a plugin therapy module and related components for the dynamic generation of therapeutic derivative stories, in accordance with an embodiment of the disclosure.

FIG. 6 is a functional block diagram illustrating a plugin therapy module 600 and related components for the dynamic generation of therapeutic derivative stories, in accordance with an embodiment of the disclosure. Therapy module 600 gathers the attribute data 605 and situational details 610 and provides these details to dynamic content creator 215 to seed the ANN select module 251 and ANN adaptation module 252 for the generation of the therapeutic derivative story. Dynamic content creator 215 uses situational details 610 and attributed data 605 to select Attribute data 605 includes characteristics that describe the content consumer. Attribute data 605 provides details for generating therapeutic derivative stories that incorporate relatable content about the content consumer and/or individuals with which the content consumer interacts. These characteristics may include names, ages, genders, culture, home location, appearance, family structure and details, friends, social structure and hierarchy, work environment and social structure, etc. Situational details 610 describe an emotional situation involving the content consumer. The emotional situation may be a struggle for which the content consumer is seeking counselling or other therapeutic help. Situational details 610 may include selection or description of a human struggle (e.g., anxiety, depression, fear, etc.) along with one or more specifics regarding the struggle. For example, situational details 610 may include details of a home or job move, a test, a public speaking event, a traumatic event (e.g., a car accident, loss of a loved one, assault, war, earthquake, etc.), or otherwise.

Therapy module 600 may acquire attribute data 605 and situational details 610 from a variety of different sources. In one embodiment, therapy module 600 may acquire some or all of attribute data 605 and situational details 610 from the end user via consumer UI 210. In other words, attribute data 605 and situational details 610 may be solicited from the end user as part of content preferences 211 and provided to therapy module 600. In one embodiment, therapy module 600 may acquire some or all of attribute data 605 and situational details 610 from a therapist (or other type of counselor) via therapist UI 615. Therapist UI 615 may provide a more sophisticated, overt interface enabling the selection of templates for populating context relevant attributes and details. Therapy module 600 may also gather attribute data 605 and situational details 610 from other connected electronic sources, should the end user grant appropriate privileges. For example, in one embodiment, therapy module 600 may access the web browser search history of the end user to acquire insight into situational details that are concerning the end user. The end user's own queries can be a window into the concerns and struggles of the end user. Therapy module 600 may also access the end user's social media accounts, emails, text messages, calendar, etc. (if permission is granted) to identify social structures, friends, family, cultural details, location, workplace, events, etc. These details can be used by dynamic content creator 215 to personalize a therapeutic derivative story, thereby controlling relatability.

Monitoring equipment 620 also provides feedback data to therapy module 600 to provide insight into how the therapeutic derivative content is impacting the content consumer. For example, monitoring equipment 620 may include one or more monitoring devices for capturing physiological responses of the content consumer while consuming the therapeutic derivative story or even while soliciting some of the initial seed data (e.g., situational details 610). Monitoring equipment 620 may include a heart rate monitor, a blood pressure monitor, a camera positioned to monitor the user's eyes, a wearable sweat detector, a galvanometer, or otherwise. Feedback from monitoring equipment 620 may be used to adjust the relatability of the therapeutic derivative story in real-time while the content consumer is watching, listening, or reading the therapeutic derivative story, or make appropriate adjustments between therapeutic sessions.

Therapy module 600 also uses attribute data 605 and situational details 610, along with feedback data from monitoring equipment 620 to determine a comfort level of the content consumer for consuming a given therapeutic derivative story. The comfort level may then be referenced by therapy module 600 to calculate a relatability score that is provided to dynamic content creator 215. The relatability score is provided to dynamic content creator 215 to adjust how relatable the therapeutic derivative story should be created for the content consumer. For example, relatability may be adjusted by modifying the realism of the therapeutic derivative story, adjusting the amount of personal characteristics or situational details incorporated into the therapeutic derivative story, or a combination of both. Feedback from monitoring equipment 620 may be used to revise the comfort level and adjust the relatability of the therapeutic derivative story in real-time while the content consumer is watching, listening, or reading the therapeutic derivative story, or make appropriate adjustments between therapeutic sessions.

Figure 7:
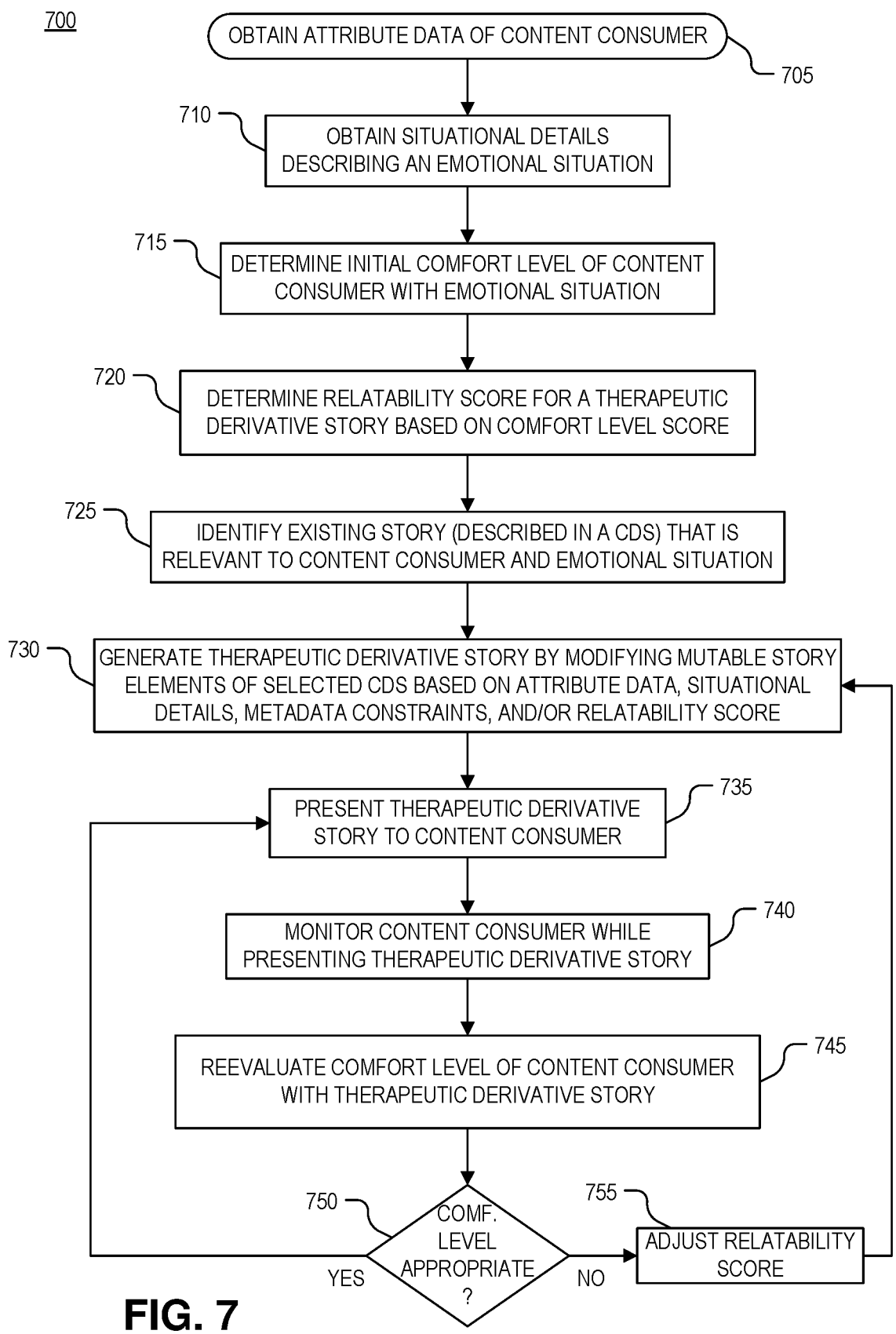
FIG. 7 is a flow chart illustrating a process for dynamic generation and adaptation of a therapeutic derivative story, in accordance with an embodiment of the disclosure.

FIG. 7 is a flow chart illustrating a process 700 for dynamic generation of a therapeutic derivative story, in accordance with an embodiment of the disclosure. The order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel.

To begin, therapy module 600 obtains attribute data 605 that describes characteristics of the content consumer (process block 705) and situational details 610 describing an emotional situation involving the content consumer (process block 710). Attribute data 605 and situational details 610 may be acquired via a variety of mechanisms including explicit solicitation from the content consumer or implicit querying via consumer UI 210. As mentioned above, these characteristics and/or details may also be acquired from a therapeutic influencer (e.g., parent, teacher, coach, clinical therapist, counselor, etc.) via therapist UI 615. Finally, some attribute data 605 may also be acquired via monitoring equipment 620. For example, if monitoring equipment 620 includes a camera and heart rate monitor, therapy module 600 may acquire likeness data along with a measure of emotional intensity associated with the emotional situation.

In a process block 715, therapy module 600 determines an initial comfort level of the content consumer with the emotional situation. This determination may be made in response to an explicit question posed to the content consumer or based upon instructions received from a therapeutic influencer via therapist UI 615. Alternatively, therapy module 600 may determine an initial comfort level based upon physiological cues measured with monitoring equipment 620. Additionally, the age, gender, or other characteristics of the content consumer along with the type of emotional situation may be considered by therapy module 600 when determining an initial comfort level. For example, some emotional situations, such as particularly traumatic or violent events, may default to a low comfort level.

In a process block 720, therapy module 600 determines a relatability score to be used by dynamic content creator 215 when generating the therapeutic derivative story. The relatability score is referenced, in connection with the metadata constraints, by the dynamic content creator 215 when determining how and to what extent to adapt mutable story elements of a CDS and associated preexisting story to match the emotional situation and/or attribute data of the content consumer. Additionally, the relatability score may be used by dynamic content creator 215 to determine how realistic and/or what medium of expression to use. For example, a low relatability score may result in the generation of a therapeutic derivative story that is expressed in the form of a cartoon storybook with few personal details. Alternatively, a high relatability score may result in the generation of a therapeutic derivative story that is expressed in the form of an immersive, realistic, first person virtual reality video with many personal characteristics and situational details incorporated. In some embodiments, the relatability score may be generated based directly on attribute data 605, situational details 610, and/or feedback data from monitoring equipment 620 without explicitly determining a comfort level.

Once attribute data 605 and situational details 610 have been obtained, dynamic content creator 215 may review library 220 and/or content marketplace 235 to identify one or more CDS 221 (or 260) that are deemed relevant to the content consumer and emotional situation (process block 725). The selected CDS 221 (or 260) along with their mutable story elements are then adapted by dynamic content creator 215 to generate the personalized therapeutic derivative story (process block 730). Attributed data 605, situational details 610, metadata constraints 232, and the relatability score may all be referenced by dynamic content creator 215 when generating the therapeutic derivative story. In particular, one or both of the metadata constraints 232 and the relatability score govern the extent to which dynamic content creator 215 adapts various mutable story elements of CDS 221 (or 260) when generating the therapeutic derivative story.

In a process block 735, the therapeutic derivative story is presented to the content consumer. While the content consumer is reading, listening, or viewing the therapeutic derivative story, therapy module 600 captures physiological responses of the content consumer via monitoring equipment 620 (process block 740). These physiological responses may include heart rate, blood pressure, sweat response, galvanic skin response, facial expressions, eye movement, or otherwise.

In a process block 745, therapy module 600 reevaluates the comfort level of the content consumer with the therapeutic derivative story. The reevaluation of the comfort level may be based upon the captured physiological responses, explicit feedback from the content consumer, a combination of these, or otherwise. For exposure therapy, the goal may be to elicit a significant emotional response from the content consumer while also maintaining a safe emotional distance so as not to provoke an emotional breakdown response (e.g., panic attack). In other therapeutic uses (e.g., issue reframing, scenario development, etc.) the content consumer's comfort level may not be as relevant and thus a fixed relatability score may be used. In such implementations, the comfort level may not be reevaluated, and process blocks 740-755 may be omitted.

In a decision block 750, if the comfort level is determined to be appropriate, then process 700 continues to present the therapeutic derivative story to the content consumer (process block 735). However, if the comfort level was adjusted in process block 745, then process 700 continues to a process block 755 where the relatability score is adjusted accordingly. The relatability score may be adjusted in real-time while the content consumer is consuming the therapeutic derivative story, or adjusted between sessions of consuming the therapeutic derivative story. When the comfort level increases, the relatability score may also be increased. Conversely, if the comfort level is reduced (e.g., the content consumer's comfort level with the therapeutic derivative story was initially set too high), then the relatability score may be reduced.

With a change in the relatability score, process 700 returns to process block 730 where dynamic content creator 215 revises one or more mutable story elements based upon the adjustments to the relatability score. For example, mutable story elements may be revised to include more attribute data 605 or situational details 610 (e.g., more personalized details) when the relatability score increases, or revised to include less attribute data 605 or situational details 610 (e.g., fewer personalized details) when the relatability score decreases. Similarly, mutable story elements may be revised to be more realistic when the relatability score increases, or revised to be less realistic when the relatability score decreases. Changes in realism may include adjusting the therapeutic derivative story between a whimsical storybook cartoon to a lifelike docudrama or first-person virtual reality. Changes in the relatability score may also result in recasting the therapeutic derivative story into a different medium of expression (e.g., textual story or comic book to audio/video expressions). Of course, these adaptations need not be mutually exclusive, but rather may be revised in unison.

Figure 8:
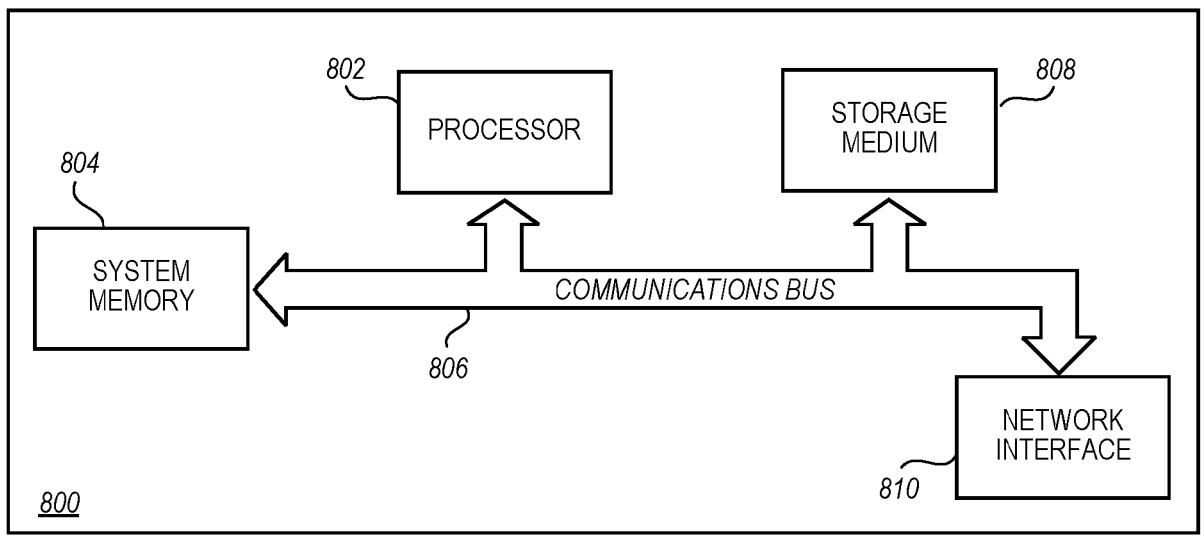
FIG. 8 is a functional block diagram illustrating a demonstrative computing device for implementing embodiments of the disclosure.

FIG. 8 is a block diagram that illustrates aspects of a demonstrative computing device appropriate for use with embodiments of the present disclosure. While FIG. 8 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 800 may be any one of any number of currently available or yet to be developed devices.

In its most basic configuration, the computing device 800 includes at least one processor 802 and a system memory 804 connected by a communication bus 806. Depending on the exact configuration and type of device, the system memory 804 may be volatile or nonvolatile memory, such as read only memory ("ROM"), random access memory ("RAM"), EEPROM, flash memory, or similar memory technology. Those of ordinary skill in the art and others will recognize that system memory 804 typically stores data and/or program modules that are immediately accessible to and/or currently being operated on by the processor 802. In this regard, the processor 802 may serve as a computational center of the computing device 800 by supporting the execution of instructions.

As further illustrated in FIG. 8, the computing device 800 may include a network interface 810 comprising one or more components for communicating with other devices over a network. Embodiments of the present disclosure may access basic services that utilize the network interface 810 to perform communications using common network protocols. The network interface 810 may also include a wireless network interface configured to communicate via one or more wireless communication protocols, such as WiFi, 2G, 3G, 4G, LTE, WiMAX, Bluetooth, and/or the like.

In the exemplary embodiment depicted in FIG. 8, the computing device 800 also includes a storage medium 808. However, services may be accessed using a computing device that does not include means for persisting data to a local storage medium. Therefore, the storage medium 808 may be omitted. In any event, the storage medium 808 may be volatile or nonvolatile, removable or nonremovable, implemented using any technology capable of storing information such as, but not limited to, a hard drive, solid state drive, CD-ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer-readable instructions, data structures, program modules, or other data. In this regard, the system memory 804 and storage medium 808 depicted in FIG. 8 are merely examples of computer-readable media.

Suitable implementations of computing devices that include a processor 802, system memory 804, communication bus 806, storage medium 808, and network interface 810 are known and commercially available. For ease of illustration and because it is not important for an understanding of the claimed subject matter, FIG. 8 does not show some of the typical components of many computing devices. In this regard, the computing device 800 may include input devices, such as a keyboard, keypad, mouse, microphone, touch input device, touch screen, tablet, and/or the like. Such input devices may be coupled to the computing device 800 by wired or wireless connections including RF, infrared, serial, parallel, Bluetooth, USB, or other suitable connections protocols using wireless or physical connections. Similarly, the computing device 800 may also include output devices such as a display, speakers, printer, etc. Since these devices are well known in the art, they are not illustrated or described further herein. Unless specifically defined herein, all terms used herein have the same meaning as they would to one skilled in the art of the present disclosure.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. At least one non-transitory computer-readable storage medium that provides instructions that, when executed by one or more machines, will cause the one or more machines to perform operations comprising:
   obtaining attribute data that describes characteristics of a content consumer;
   obtaining situational details describing an emotional situation involving the content consumer;
   determining a relatability score for a therapeutic derivative story to aid the content consumer in understanding or adapting to the emotional situation;
   selecting a content data structure (CDS) from a library of CDS based on the attribute data or the situational details, the CDS specifying story elements of a preexisting story, the story elements defined at one or more different levels of story abstraction and associated with metadata constraints that constrain a modification or a use of the story elements within the therapeutic derivative story, wherein at least some of the metadata constraints indicate whether associated ones of the story elements are mutable story elements, wherein at least one of the mutable story elements of the selected CDS includes a character or an object identified from the preexisting story using computational image or shape recognition on a picture or a video frame from a fixed expression of the preexisting story;
   adapting one or more of the mutable story elements based on the attribute data or the situational details as constrained by the metadata constraints and to an extent determined at least in part by the relatability score to generate the therapeutic derivative story; and
   rendering the therapeutic derivative story for presentation to the content consumer.

2. The at least one non-transitory computer-readable storage medium of claim 1, wherein the operations further comprise:
   determining a comfort level of the content consumer for consuming the therapeutic derivative story; and
   setting the relatability score used to adapt the mutable story elements based upon the comfort level.

3. The at least one non-transitory computer-readable storage medium of claim 2, wherein the comfort level is initially selected based upon the attribute data and the situational details.

4. The at least one non-transitory computer-readable storage medium of claim 2, wherein the comfort level is initially selected based upon inputs from the content consumer or a therapeutic influencer of the content consumer.

5. The at least one non-transitory computer-readable storage medium of claim 1, wherein the operations further comprise:
   capturing physiological responses of the content consumer with monitoring equipment while presenting the derivative therapeutic story to the content consumer; and
   adjusting the relatability score based upon the physiological responses captured with the monitoring equipment after presenting at least a portion of the therapeutic derivative story,
   wherein adapting the one or more of the mutable story elements includes revising one or more of the mutable story elements to reflect the adjustment to the relatability score.

6. The at least one non-transitory computer-readable storage medium of claim 5, wherein the monitoring equipment comprises a camera positioned to monitor the content consumer's eyes, a heart rate monitor, a blood pressure monitor, a wearable sweat detector, or a galvanometer.

7. The at least one non-transitory computer-readable storage medium of claim 5, wherein revising the one or more of the mutable story elements to reflect the adjustment to the relatability score comprises:
   revising the one or more of the mutable story elements to include more of the characteristics of the content consumer or more of the situational details, when the relatability score is increased; and
   revising the one or more of the mutable story elements to include less of the characteristics of the content consumer or less of the situational details, when the relatability score is decreased.

8. The at least one non-transitory computer-readable storage medium of claim 5, wherein revising the one or more of the mutable story elements to reflect the adjustment to the relatability score comprises:
   revising the one or more of the mutable story elements to be more realistic, when the relatability score is increased; and
   revising the one or more of the mutable story elements to be less realistic, when the relatability score is decreased.

9. The at least one non-transitory computer-readable storage medium of claim 5, wherein revising the one or more of the mutable story elements to reflect the adjustment to the relatability score comprises revising the one or more of the mutable story elements in real-time while the content consumer is consuming the therapeutic derivative story.

10. The at least one non-transitory computer-readable storage medium of claim 1, wherein adapting the one or more mutable story elements comprises:
    feeding the content data structure along with the attribute data and the situational details into an artificial neural network; and
    modifying the one or more mutable story elements with the artificial neural network based upon the metadata constraints and portions of the attribute data and the situational details.

11. The at least one non-transitory computer-readable storage medium of claim 10, wherein the artificial neural network comprises one of a generative adversarial network (GAN) or a variational autoencoder.

12. A computer implemented method for dynamic generation of a therapeutic derivative story, the method comprising:

obtaining attribute data that describes characteristics of a content consumer;

obtaining situational details describing an emotional situation involving the content consumer;

determining a relatability score for the therapeutic derivative story to aid the content consumer in understanding or adapting to the emotional situation;

selecting a content data structure (CDS) from a library of CDS based on the attribute data or the situational details, the CDS specifying story elements of a preexisting story, the story elements defined at one or more different levels of story abstraction and associated with metadata constraints that constrain a modification or a use of the story elements within the therapeutic derivative story, wherein at least some of the metadata constraints indicate whether associated ones of the story elements are mutable story elements, wherein at least one of the mutable story elements of the selected CDS includes a character or an object identified from the preexisting story using computational image or shape recognition on a picture or a video frame from a fixed expression of the preexisting story;

adapting one or more of the mutable story elements based on the attribute data or the situational details as constrained by the metadata constraints and to an extent determined at least in part by the relatability score to generate the therapeutic derivative story; and rendering the therapeutic derivative story for presentation to the content consumer.

13. The computer implemented method of claim 12, wherein the operations further comprise:

determining a comfort level of the content consumer for consuming the therapeutic derivative story; and setting the relatability score used to adapt the mutable story elements based upon the comfort level.

14. The computer implemented method of claim 13, wherein the comfort level is initially selected based upon the attribute data and the situational details.

15. The computer implemented method of claim 13, wherein the comfort level is initially selected based upon inputs from the content consumer or a therapeutic influencer of the content consumer.

16. The computer implemented method of claim 13, wherein the operations further comprise:

adjusting the relatability score based upon feedback from the content consumer after consuming at least a portion of the therapeutic derivative story, and wherein adapting the one or more of the mutable story elements includes revising one or more of the mutable story elements to reflect the adjustment to the relatability score.

17. The computer implemented method of claim 16, wherein the operations further comprise:

capturing physiological responses of the content consumer while presenting the derivative therapeutic story to the content consumer, wherein the feedback comprises the physiological responses.

18. The computer implemented method of claim 16, wherein revising the one or more of the mutable story elements to reflect the adjustment to the relatability score comprises:

revising the one or more of the mutable story elements to include more of the characteristics of the content consumer or more of the situational details, when the relatability score is increased; and revising the one or more of the mutable story elements to include less of the characteristics of the content consumer or less of the situational details, when the relatability score is decreased.

19. The computer implemented method of claim 16, wherein revising the one or more of the mutable story elements to reflect the adjustment to the relatability score comprises:

revising the one or more of the mutable story elements to be more realistic, when the relatability score is increased; and revising the one or more of the mutable story elements to be less realistic, when the relatability score is decreased.

20. The computer implemented method of claim 16, wherein revising the one or more of the mutable story elements to reflect the adjustment to the relatability score comprises revising the one or more of the mutable story elements in real-time while the content consumer is consuming the therapeutic derivative story.

21. The computer implemented method of claim 12, wherein adapting the one or more mutable story elements comprises:

feeding the content data structure along with the attribute data and the situational details into an artificial neural network; and modifying the one or more mutable story elements with the artificial neural network based upon the metadata constraints and portions of the attribute data and the situational details.

* * * * *